United States Patent [19]
Baumann et al.

[11] 3,985,376
[45] Oct. 12, 1976

[54] DYE PRECURSORS FOR PRESSURE-SENSITIVE RECORDING MATERIAL

[75] Inventors: Hans Baumann, Ludwigshafen; Andreas Oberlinner, Mannheim, both of Germany

[73] Assignee: BASF Aktiengesellschaft, Ludwigshafen (Rhine), Germany

[22] Filed: Mar. 13, 1975

[21] Appl. No.: 558,148

[30] Foreign Application Priority Data
June 7, 1972 Germany ..........................2227597

Related U.S. Application Data

[63] Continuation of Ser. No. 366,497, June 4, 1973, abandoned.

[52] U.S. Cl. ................... 282/27.5; 260/296 R; 427/150; 428/537; 428/914
[51] Int. Cl.² .......................................... B41M 5/22
[58] Field of Search .......... 282/27.5; 428/411, 537, 428/195, 199, 211, 306, 307, 323, 326, 914; 427/146, 150, 151; 260/295 R, 296 R

[56] References Cited
UNITED STATES PATENTS 3,485,847  12/1969  Bossert et al. ............... 260/295.5 R
3,488,359  1/1970  Bossert et al. ............... 260/295.5 R FOREIGN PATENTS OR APPLICATIONS
47-8014  3/1972  Japan................... 427/146

OTHER PUBLICATIONS

Migachev et al., Chem. Abstracts, vol. 69(23), 96408n, 12-2-68.

Kost et al., Chem. Abstracts, vol. 61(7), 8271-c, 9-28-64.

Krivum et al., Chem. Abstracts, vol. 73(19), 98769n, 11-9-70.

*Primary Examiner*—Thomas J. Herbert, Jr.
*Assistant Examiner*—Bruce H. Hess
*Attorney, Agent, or Firm*—Johnston, Keil, Thompson & Shurtleff

[57] ABSTRACT

Use of a 4-(4'-aminophenyl)-pyridine as a dye-forming component for a pressure-sensitive recording material.

6 Claims, No Drawings

DYE PRECURSORS FOR PRESSURE-SENSITIVE RECORDING MATERIAL

This is a continuation, of application Ser. No. 366,497 filed June 4, 1973 now abandoned.

The invention relates to the use of a 4-(4'-aminophenyl)-pyridine of the formula (I):

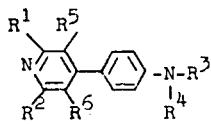

in which
R[1] and R[2] are hydrogen or alkyl or aryl of one to eight carbon atoms which may bear alkoxy or halogen as a substituent;
R[3] is hydrogen or alkyl of one to five carbon atoms;
R[4] is alkyl, haloalkyl, cyanalkyl, aryl or aralkyl of one to eight carbon atoms which may bear alkoxy as a substituent;
R[5] and R[6] are hydrogen or carbalkoxy of two to five carbon atoms and R[3] and R[4] may be closed to form a ring as a chromogenic material or dye-forming component for a pressure-sensitive recording material.

The following are examples of specific radicals:
for R[1] and R[2]: (besides hydrogen) methyl, ethyl, isopropyl, butyl, phenyl, p-methoxyphenyl, p-ethoxyphenyl, γ-methoxypropyl and p-chlorophenyl, of which hydrogen and phenyl are particularly preferred;
for R[3]: hydrogen, methyl, ethyl, propyl and butyl, of which methyl, ethyl and n-butyl are preferred;
for R[4]: methyl, ethyl, propyl, butyl, β-chloroethyl, β-cyanoethyl, phenyl, benzyl, p-methoxyphenyl and p-ethoxyphenyl of which methyl, ethyl, n-propyl and phenyl are preferred;
for R[5] and R[6] (besides hydrogen): carbomethoxy, carboethoxy, carbopropoxy and carbobutoxy of which carboethoxy is preferred.

The 4-(4'-aminophenyl)-pyridines of the formula (I) may be prepared by conventional methods, for example by condensation of 4-(4'-aminophenyl)-pyrylium salts with ammonia or agents which disengage ammonia or by condensation of a 4-aminobenzaldehyde of the formula:

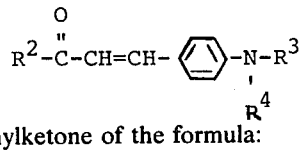

or an arylvinylketone of the formula:

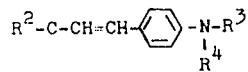

with a ketone of the formula $R^1\text{-CO-CH}_3$ in the presence of ammonia or an agent which disengages ammonia. Examples of preferred starting materials are therefore:

as 4-aminobenzoaldehydes:
4-dimethylaminobenzaldehyde, 4-diethylaminobenzaldehyde,
4-N-methyl-N-(4'-ethoxyphenyl)-aminobenzaldehyde and
4-N-methyl-N-(β-chloroethyl)-aminobenzaldehyde as well
as 4-N-morpholinobenzaldehyde;
as arylvinyl ketones:
4-dimethylaminobenzal acetone,
4-diethylaminobenzal acetone,
4-N-methyl-N-(β-cyanoethyl)-aminobenzal acetophenone,
4-dimethylaminobenzal acetophenone,
4'-chloro-4-diethylaminobenzal acetophenone,
4'-methoxy-4-dimethylaminobenzal acetophenone;
as ketones of the formula $R^1\text{-CO-CH}_3$:
acetone, acetophenone, 4-methoxyacetophenone and 4-chloroacetophenone.

Compounds of the formula (I) in which there are no substituents in the pyridine nucleus (R[1], R[2], R[5] and R[6] being hydrogen) may also be prepared by a conventional method by condensation of an aniline derivative with pyridine in the presence of benzoyl chloride with or without copper powder. Examples of aniline derivatives are: N,N-dimethylaniline, N,N-diethylaniline, N-methyl-N-benzylaniline, N-methyl-N-(β-cyanoethyl)-aniline, and N-methyldiphenylamine.

The following are literature references which are relevant to the production of dye precursors:
Ann, 509 (1934) 142: J. Amer. Chem. Soc., 74 (1952) 200 and 3605, Zurnal Obscei Chimii, 38 (1968) 1368 and Ber. 90 (1957) 789.

The 4-(4'-aminophenyl)-pyridines of the formula (I) are pale yellow to colorless compounds. When dissolved in non-polar or only weakly polar solvents such as hydrocarbons, chlorohydrocarbons or esters they give intense yellow to orange colorations upon the addition of an acid substance. This reaction, which is also caused by kaolin, zeolites, bentonite, silicic acid, alum, zinc sulfate, oxalic acid and phenolic condensation products, renders the compounds suitable as dye precursors for pressure-sensitive recording materials, particularly for the production of copying papers. Pressure-sensitive materials of the said type may be prepared for example by applying the dye precursor together with a binder to a substrate. In particular the compounds, if desired mixed with other dye precursors such as crystal violet lactone, N-phenyl-leucoauramine, N-benzoyl-leucomethylene blue, may be encapsulated in dissolved form in microcapsules and the capsules applied together with the binder to paper. A visible trace occurs in contact with another surface having an acid reaction when pressure is applied sufficient to rupture the capsules.

The following Examples illustrate the invention. The parts and percentages specified are by weight.

EXAMPLE 1

158 parts of pyridine and 155 parts of benzoyl chloride are heated with 4 parts of copper powder for an hour at 100° to 105° C. At 70° to 80° C there is then added 197 parts of methylbenzylaniline and heating is continued for another five hours at 100° to 105° C. When the reaction is over 800 parts of toluene is added at 70° to 80° C, and the precipitate is suction filtered and dissolved in 1,000 parts of 5% hydrochloric acid. The product is clarified with animal charcoal and reprecipitated in the cold with ammonia and recrystalized from a mixture of ethanol and water for further purification. 50 parts of 4-(4'-methylbenzylaminophenyl)-pyridine is obtained as practically colorless crystals which melt at 118° to 119° C.

The compound is dissolved in chlorinated diphenyl, encapsulated in microcapsules and brushed with a binder onto the surface of paper. In contact with an acid receptive layer a greenish yellow trace is obtained.

EXAMPLE 2

75 parts of p-dimethylaminobenzaldehyde and 125 parts of acetophenone together with 500 parts of ammonium acetate are heated in 1,000 parts of glacial acetic acid for four hours under reflux. The precipitate deposited after standing for twelve hours at room temperature is suction filtered and recrystallized from 500 parts of ethanol. 57 parts of a pale yellow compound (2,6-diphenyl-4-(4'-dimethylaminophenyl)-pyridine) is obtained which has a melting point of 128° to 129° C.

The compound is dissolved in chloroparaffin, enclosed within microcapsules and applied to the surface of paper together with a binder. Upon writing in contact with an acid receptive material a yellowish orange trace is obtained.

The 4-(4'-aminophenyl)-pyridines hereinafter characterized by reference to the radicals $R^1$ to $R^6$ in their constitution, by their melting point and by the color which is formed by reaction with acid substances, may be obtained by a method analogous to that described in Example 1 or 2.

EXAMPLE 3

$R^1 = H$; $R^2 = H$; $R^3 = CH_3$; $R^4 = CH_3$; $R^5 = H$; $R^6 = H$; melting point: 235° to 237° C; color: greenish yellow.

EXAMPLE 4

$R^1$, $R^2$, $R^5$ and $R^6 = H$; $R^3 = CH_3$; $R^4 = C_2H_5$; melting point 154° C; color: greenish yellow.

EXAMPLE 5

$R^1$, $R^2$, $R^5$ and $R^6 = H$; $R^3$ and $R^4 = C_2H_5$; melting point 156° to 158° C; color: greenish yellow.

EXAMPLE 6

$R^1$, $R^2$, $R^5$ and $R^6 = H$; $R^3 = CH_3$; $R^4 = n-C_3H_7$; melting point 123° C; color: greenish yellow.

EXAMPLE 7

$R^1$, $R^2$, $R^5$ and $R^6 = H$; $R^3$ and $R^4 = n-C_4H_9$; melting point 156° to 157° C; color: greenish yellow.

EXAMPLE 8

$R^1$, $R^2$ and $R^4 = C_6H_5$; $R^3 = CH_3$; $R^5$ and $R^6 = H$; melting point 136° to 138° C; color: orange.

EXAMPLE 9

$R^1$ and $R^2 = C_6H_5$; $R^3 = CH_3$; $R^4 = p-C_6H_4-OC_2H_5$; $R^5$ and $R^6 = H$; melting point 144° to 145° C; color: orange.

EXAMPLE 10

$R^1$ and $R^2 = p-C_6H_4-OCH_3$; $R^3$ and $R^4 = CH_3$; $R^5$ and $R^6 = H$; melting point 130° to 131° C; color: orange.

EXAMPLE 11

$R^1$, $R^2$, $R^3$ and $R^4 = CH_3$; $R^5$ and $R^6 = CO_2C_2H_5$; melting point 124° to 125° C; color: yellow.

We claim:

1. A pressure-sensitive recording material which comprises a paper substrate coated with a dye-forming component and a binder, said dye-forming component being a 4-(4'aminophenyl)pyridine of the formula:

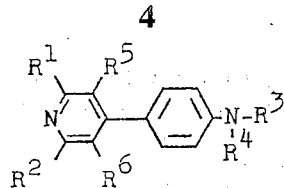

in which
$R^1$ and $R^2$ are hydrogen, methyl, ethyl, propyl, butyl, phenyl, p-methoxyphenyl, p-ethoxyphenyl, γ-methoxypropyl or p-chlorophenyl,
$R^3$ is hydrogen, methyl, ethyl, propyl or butyl,
$R^4$ is methyl, ethyl, propyl, butyl, β-chloroethyl, β-cyanoethyl, phenyl, benzyl, p-methoxyphenyl or p-ethoxyphenyl, and
$R^5$ and $R^6$ are hydrogen, carbomethoxy, carboethoxy, carbopropoxy or carbobutoxy.

2. A pressure-sensitive recording material as claimed in claim 1, wherein in the dye-forming component
$R^1$ and $R^2$ are hydrogen, methyl, phenyl or p-methoxyphenyl,
$R^3$ is methyl, ethyl, propyl, or butyl,
$R^4$ is methyl, ethyl, propyl, butyl, phenyl, benzyl, p-methoxyphenyl, or p-ethoxphenyl, and
$R^5$ and $R^6$ are hydrogen, carbomethoxy or carbethoxy.

3. A pressure-sensitive recording material as claimed in claim 1, wherein in the dye-forming component
$R^1$ and $R^2$ are hydrogen or phenyl,
$R^3$ and $R^4$ are methyl, ethyl, propyl or butyl, and
$R^5$ and $R^6$ are hydrogen.

4. A pressure-sensitive recording material as claimed in claim 1, wherein the dye-forming component has the formula:

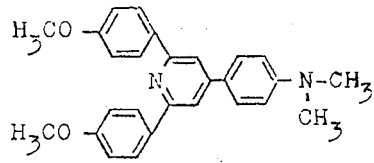

5. A pressure-sensitive recording material as claimed in claim 1, wherein the dye-forming component has the formula:

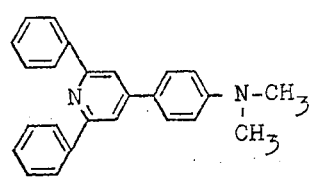

6. A pressure-sensitive recording material as claimed in claim 1, wherein the dye-forming component has the formula:

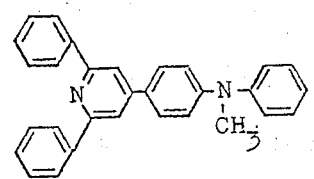

* * * * *